US00PP17500P2

(12) United States Plant Patent
Austin

(10) Patent No.: US PP17,500 P2
(45) Date of Patent: Mar. 13, 2007

(54) SHRUB ROSE PLANT NAMED 'AUSRUMBA'

(50) Latin Name: *Rosa hybrida*
Varietal Denomination: AUSrumba

(75) Inventor: David C. H. Austin, Wolverhampton (GB)

(73) Assignee: David Austin Roses Limited, Wolverhampton (GB)

( * ) Notice: Subject to any disclaimer, the term of this patent is extended or adjusted under 35 U.S.C. 154(b) by 0 days.

(21) Appl. No.: 11/263,886

(22) Filed: Oct. 31, 2005

(51) Int. Cl.
*A01H 5/00* (2006.01)

(52) U.S. Cl. ..... Plt./107

(58) Field of Classification Search ..... Plt./107, Plt./102, 104
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Shrub rose plant substantially as herein shown and described, characterized particularly by its shallow-cupped flowers of pure pink paling to soft blush on the outside with strong Old Rose fragrance with hints of myrrh on a rounded shrub of medium height with arching stems; and disease resistance.

1 Drawing Sheet

Figure 1:
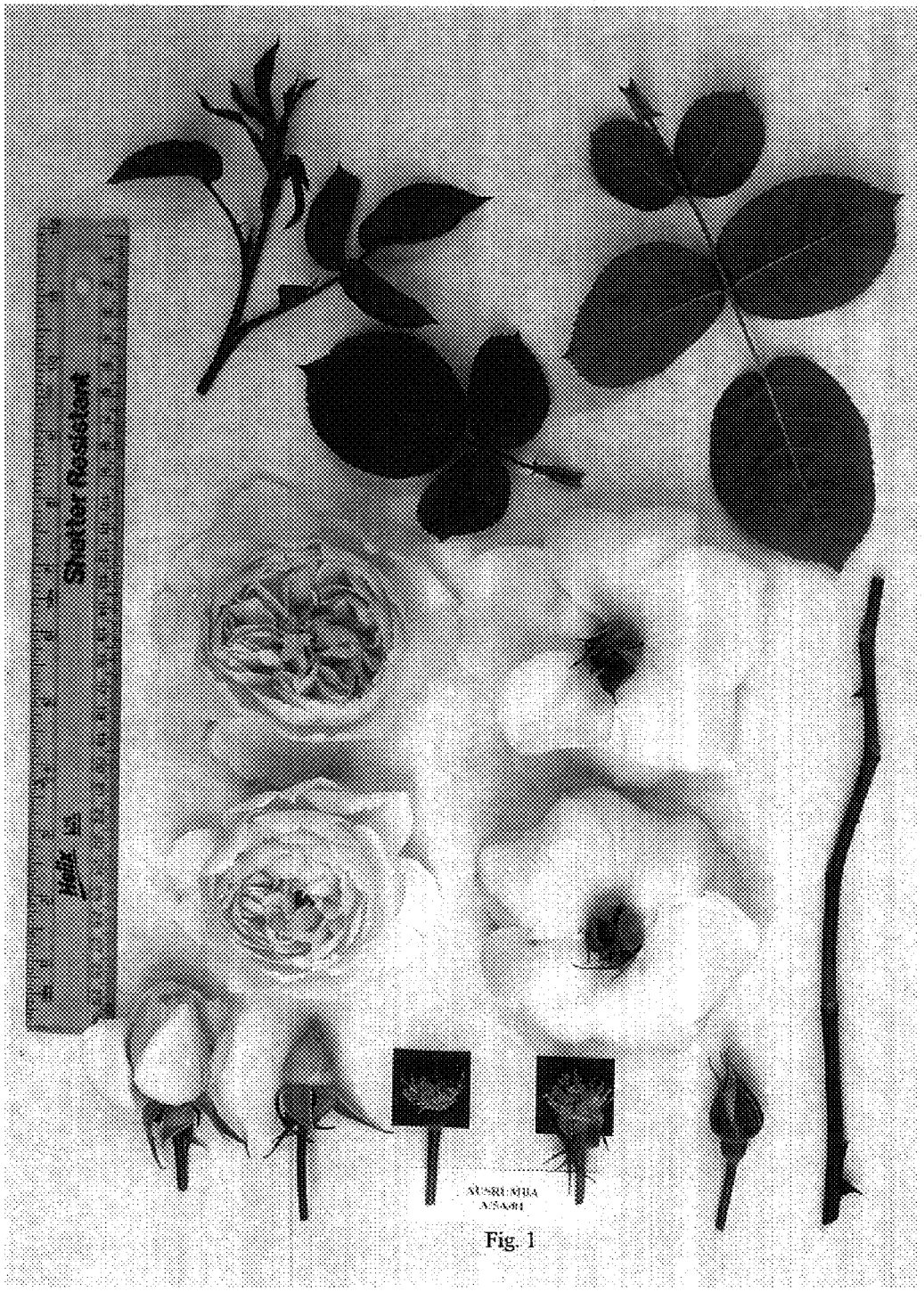

Genus and species: *Rosa hybrida.*
Variety denomination: 'AUSrumba'.

ORIGIN OF THE INVENTION

The present invention relates to a new and distinct variety of a shrub rose plant named 'AUSrumba' which was originated by me by crossing an unnamed, unpatented seedling with an unnamed, unpatented seedling.

BACKGROUND OF THE INVENTION

The primary objective of this breeding was to produce a very free-flowering and healthy variety, having pale pink, cupped blooms and a strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Shallow-cupped flowers of pure pink paling to soft blush on the outside.
2. Rounded shrub of medium height with arching stems.
3. Strong Old Rose fragrance with hints of myrrh.

Asexual reproduction of this new variety by budding, as performed at Albrighton, England, shows that the foregoing and all other characteristics and distinctions come true to form and are established and transmitted through succeeding propagations.

Comparison with Parents

The seed parent has paler green foliage and yellow blooms compared with the pale pink blooms of 'AUSrumba'. The pollen parent is a shorter shrub with more upright growth than 'AUSrumba' and a less formal petal arrangement.

Comparison with Similar Variety

'AUSham' (U.S. Plant Pat. No. 11,421) has fuller, but smaller blooms than 'AUSrumba' and makes a larger shrub. 'AUSham' also has fewer thorns than 'AUSrumba'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character. The reference A/5A/01 appearing beneath the varietal name on the illustration is the applicant's breeding code for the cultivar.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at one year of age grown in a garden environment at Albrighton, England.

Blooming habit: Recurrent. The number of blooms per plant during the growing season is profuse, but there are too many to count.

Bud:
*Size.*—About 3.2 cm long and 2.2 cm in diameter when the petals start to unfurl.
*Form.*—The bud form is pointed ovoid.

*Color.*—When sepals first divide, bud color is Red Group 38C. When half blown, the upper sides of the petals are White Group 155D and Red Group 55C on margin; and the lower sides of the petals are White Group 155D and Red Group 52D on margin.

*Sepals.*—Color: Lower surface: Green Group 143A overlaid with Greyed-Purple Group 185A. Upper surface: Green Group 138B with spots of Greyed-Red Group 182A. Length: 3.5 cm. Width: 1.2 cm. Shape: Subulate. Surface texture: Upper surface: Pubescent. Lower surface: Smooth. There are three lightly appendaged sepals. There are two unappendaged sepals with canescent edges.

*Receptacle.*—Color: Yellow-Green Group 144A with shading of Greyed-Purple Group 183C. Shape: Campanulate. Size: Medium, about 1.1 cm long×1.1 cm wide. Surface: Smooth.

*Peduncle.*—Length: Long, averaging about 13 cm. Surface: Glandular. Color: Yellow-Green Group 144A (with tint of dark red, not concentrated enough to determine RHS color code). Strength: Strong.

Bloom:

*Size.*—Large. Average open diameter is about 9.65 cm.

*Borne.*—In rounded shape clusters of five to seven blooms.

*Form.*—When first open: Cupped. Permanence: Retains its form.

*Petalage.*—Number of petals under normal conditions: 90–100.

*Color.*—The upper sides of the petals are Red Group 56C around margin fading to White Group 155D in center. The reverse sides of the petals are Red Group 56D around margin fading to White Group 155D in center. The bases of the petals are Yellow Group 8B. The major color on the upper side is Red Group 56D around margin fading to White Group 155D in center.

*Variegations.*—None.

*Discoloration.*—The general tonality at the end of the first day: Red Group 56D and White Group 155D. At the end of the third day: Red Group 56D and White Group 155B.

*Fragrance.*—Strong, Old Rose, hint of myrrh.

Petals:

*Texture.*—Velvety.

*Size.*—Width: 3.4 cm. Length: 4.6 cm.

*Surface.*—Smooth.

*Shape.*—Obovate (inner), obcordate (outer). Margin: Some flat, some lacerate. Apex Shape: Some obtuse, some obcordate. Base Shape: Cuneate. Form: Incurved.

*Arrangement.*—Imbricated, regularly arranged, shingle-like.

*Petaloids.*—Number: 6. Shape: Fine filament, joined to a petal of small size, anther fused to petal. Anther: Length: 1 mm. Color: Yellow-Orange Group 12C. Filament: Length: 6 mm. Color: Yellow-Orange Group 17C. Petal: Length: 18 mm. Color: Red Group 56C.

*Persistence.*—Petals drop off cleanly before drying.

*Lastingness.*—On the plant: Short (about 3 days). As a cut flower: Short (about 4 days).

Reproductive parts:

*Stamens.*—Number: 70. Length: 8 mm. Anthers: Length: 2 mm. Color: Yellow-Orange Group 17B. Arrangement: Regular around styles, some tucked in calyx or partly so; mixed with petaloids. Filaments: Color: Yellow-Orange Group 15C. Length: 6 mm. Pollen: Color: Yellow-Orange Group 17B.

*Pistils.*—Number: 69. Length: 10 mm. Styles: Color: Yellow Group 2D with touch of Red Group 48B under stigma. Length: 9 mm. Stigmas: Color: Yellow Group 8B. Length: 1 mm.

*Hips.*—None observed.

PLANT

*Form.*—Shrub.

*Growth.*—Vigorous, bushy.

*Age at maturity.*—Two years.

*Mature plant.*—Height: 1.25 m. Width: 0.9 m.

*Rootstock.*—'Dr. Huey' in the USA *Rosa dumetorum* 'Laxa' for the observed plants in the U.K.

Foliage: Number of leaflets on normal mid-stem leaves: 5, including terminal leaflet.

*Size.*—Large. About 18.8 cm long×13.1 cm wide.

*Quantity.*—Normal. Average number leaves per flowering stem: 12.

*Color.*—New foliage: Upper side: Green Group 137C, with Greyed-Purple Group 185A along margin and serrations. Lower side: Yellow-Green Group 146B, overlaid with Greyed-Purple Group 185B. Old foliage: Upper side: Green Group 139A. Lower side: Green Group 137C.

Leaflets:

*Size.*—About 7.4 cm long×5.5 cm wide.

*Shape.*—Ovate.

*Base shape.*—Cordate.

*Apex shape.*—Acuminate.

*Texture.*—Smooth.

*Edge.*—Serrated.

*Serrations.*—Single.

*Petiole.*—Color: Yellow-Green Group 144A. Surface texture: Smooth. Length: 7 cm. Width: 2 mm.

*Petiole rachis.*—Color: Yellow-Green Group 145B. Underside: Smooth.

*Stipules.*—Length: 2.2 cm; margin glandular. Color: Yellow-Green Group 146B.

*Auricle shape.*—Subulate.

*Disease resistance.*—Resistant to powdery and downy mildew, blackspot and rust in normal growing conditions.

*Rest resistance.*—Not tested.

*Vein color.*—Yellow-Green Group 145B.

*Venation pattern.*—Reticulate.

Wood:

*New wood.*—Color: Greyed-Purple Group 185A. Bark: Smooth.

*Old wood.*—Color: Yellow-Green Group 146B. Bark: Smooth.

Stems:

*Mature stem.*—Length: 60 cm. Diameter: 7 mm.

*Internode distance.*—4.5 cm. The above measurements are all variable, depending on growing conditions in a season.

Prickles:

*Quantity.*—On main canes from base: 6 per 5 cm stem length. On laterals from main canes: 6 per 5 cm stem length.

*Form.*—Concave curved inward.

*Length.*—9 mm.

*Color when young.*—Greyed-Purple Group 183A.

*Color when mature.*—Greyed-Purple Group 183A.

Small prickles:

*Quantity.*—On main stalks: Number per stem length: 9 per 5 cm. On laterals: Number per stem length: 6 per 5 cm.

*Color.*—Greyed-Purple Group 183A.

Winter hardiness: Not tested.

I claim:

1. A new and distinct variety of shrub rose plant substantially as herein shown and described, characterized particularly by its shallow-cupped flowers of pure pink paling to soft blush on the outside with strong Old Rose fragrance with hints of myrrh on a rounded shrub of medium height with arching stems; and disease resistance.

* * * * *